United States Patent [19]

Thomas et al.

[11] Patent Number: 5,536,655
[45] Date of Patent: Jul. 16, 1996

[54] GENE CODING FOR THE E1 ENDOGLUCANASE

[75] Inventors: Steven R. Thomas, Denver; Robert A. Laymon; Michael E. Himmel, both of Littleton, all of Colo.

[73] Assignee: Midwest Research Institute, Kansas City, Mo.

[21] Appl. No.: 276,213

[22] Filed: Jul. 15, 1994

Related U.S. Application Data

[63] Continuation-in-part of Ser. No. 125,115, Sep. 21, 1993, Pat. No. 5,366,884, which is a continuation-in-part of Ser. No. 826,089, Jan. 27, 1992, Pat. No. 5,275,944, which is a continuation-in-part of Ser. No. 412,434, Sep. 26, 1989, Pat. No. 5,110,735.

[51] Int. Cl.$^6$ .............. C12N 9/42; C12N 1/20; C12P 21/06; C07H 19/00
[52] U.S. Cl. .......... 435/209; 435/69.1; 435/252.3; 435/252.31; 435/252.33; 435/253.5; 435/254.21; 435/320.1; 536/22.1; 536/23.1; 536/23.2; 536/23.7
[58] Field of Search .................... 435/69.1, 209, 435/252.3, 252.31, 252.33, 253.5, 254.21, 320.1; 536/22.1, 23.1, 23.2, 23.7

[56] References Cited

U.S. PATENT DOCUMENTS

| | | | |
|---|---|---|---|
| 5,110,735 | 5/1992 | Tucker et al. | 435/209 |
| 5,275,944 | 1/1944 | Himmel et al. | 435/209 |
| 5,366,884 | 11/1994 | Adney et al. | 435/209 |

OTHER PUBLICATIONS

Mohagheghi et al., *Int. J. System. Bacteriol.*, 36:435–443 (1986).

Lejeune et al., *Biosynthesis and Biodegradation of Cellulose*, C. Haigler and P. J. Weimer, Ed., Marcel–Dekker, NY 1991, pp. 623–672.

*Primary Examiner*—Charles L. Patterson, Jr.
*Assistant Examiner*—Hyosuk Kim
*Attorney, Agent, or Firm*—Edna M. O'Connor; Ruth Eure

[57] ABSTRACT

The gene encoding *Acidothermus cellulolyticus* E1 endoglucanase is cloned and expressed in heterologous microorganisms. A new modified E1 endoglucanase enzyme is produced along with variants of the gene and enzyme. The E1 endoglucanase is useful for hydrolyzing cellulose to sugars for simultaneous or later fermentation into alcohol.

18 Claims, 6 Drawing Sheets

FIG. 1

|  | 10 | 20 | 30 | 40 | 50 |  |
|---|---|---|---|---|---|---|
|  | 1234567890 | 1234567890 | 1234567890 | 1234567890 | 1234567890 |  |
| | vpralrrvpg | srvmlrvgvv | vavlalvaal | anlavprpar | aAGGGYWHTS | 50 |
| | GREILDANNV | PVRIAGINWF | GFETCNYVVH | GLWSRDYRSM | LDQIKSLGYN | 100 |
| | TIRLPYSDDI | LKPGTMPNSI | NFYQMNQDLQ | GLTSLQVMDK | IVAYAGQIGL | 150 |
| | RIILDRHRPD | CSGQSALWYT | SSVSEATWIS | DLQALAQRYK | GNPTVVGFDL | 200 |
| | HNEPHDPACW | GCGDPSIDWR | LAAERAGNAV | LSVNPNLLIF | VEGVQSYNGD | 250 |
| | SYWWGGNLQG | AGQYPVVLNV | PNRLVYSAHD | YATSVYPQTW | FSDPTFPNNM | 300 |
| | PGIWNKNWGY | LFNQNIAPVW | LGEFGTTLQS | TTDQTWLKTL | VQYLRPTAQY | 350 |
| | GADSFQWTFW | SWNPDSGDTG | GILKDDWQTV | DTVKDGYLAP | IKSSIFDPVG | 400 |
| | ASASPSSQPS | PSVSPSPSPS | PSASRTPTPT | PTPTASPTPT | LTPTATPTPT | 450 |
| | ASPTPSPTAA | SGARCTASYQ | VNSDWGNGFT | VTVAVTNSGS | VATKTWTVSW | 500 |
| | TFGGNQTITN | SWNAAVTQNG | QSVTARNMSY | NNVIQPGQNT | TFGFQASYTG | 550 |
| | SNAAPTVACA | AS | | | | 562 |

FIG. 2

```
E1 Cat Domain    ---------- ---------- ---------- ----AGGGYWE TSGRETLDAN    17
GUN_BACPO        MKKKGLKKTF FVIASLVMGF TLYGYTPVSA DAASVKGYYH TQGNKLMDES      50
GUNA_XANCP_CAT   ---------- ---------- ---------- -------YSI NNSRCLMDDS     13
Consensus        .......... .......... .......... ........Y. .....L.D.S     50

E1 Cat Domain    NVPVRIAGIN WFGFETLNYV VAGLWSRDYR SNLDQIKSLG VNLIRLPYSD    67
GUN_BACPO        GKEAAFNGIN WFGIETLNYT IHGLWFRSMD LMLLQVKKEG YNLIRLPYSN    100
GUNA_XANCP_CAT   GKVVQLRGMN MEGLETLNHV MGGLWWRNWK DMIVQMQGLG LNAVRLPFCP    63
Consensus        .......G.N W.G.ETL.... ..GLW.R... ......... G.N..RLP...    100

E1 Cat Domain    DILKPGTMEN SINFYQMNLQ LLGLTSLKWH DKLVAYAGQI GLRILLDRHR    117
GUN_BACPO        QLFDSSSRND SIDY-HKNLD LVGLNPIQLM DKLIEKAGQR GIQILLDRHR    149
GUNA_XANCP_CAT   ATLRSDIMPA SIDY-SRNAD LCGLTSIQLL DKVIAEFNAR GMYVLLDHHT    112
Consensus        .......... SI....N.. L.GL........ DK........ G....LD...    150

E1 Cat Domain    PDCSGISHLW YISSVSEATW LSDLQAIAER YKGNPIVMGF DLHNEPHDEA    167
GUN_BACPO        PGSGGQSFLW YTSQYFESRW ISDWKMLALR YKNNPIVMGA DLHNEPHGCA    199
GUNA_XANCP_CAT   PDCAGISHLW YTGSYTEACW LADLRFVANR YKNVPMVLGL DLKNEPHGAA    162
Consensus        P...G.S.LW Y.........W ..D...... YKN.P.V.G. DL.NEPH..A    200

E1 Cat Domain    QWGTGDPSID WRIAALRAGN AMGKVNPNLI IFVEGVQSY- ----NGDSYW    213
GUN_BACPO        SWGIGNASID WRIAAKRAGN AIGVLNPNWL ILVEGVDHN- VQGNNSQYWW    248
GUNA_XANCP_CAT   TWGIGNAATD WNKAALRGSA AMGIVAPKWL IAVEGTTDNP VCSTNGGIFW    212
Consensus        .WG.G..... W..AA.R.GN A.G.V.P... I.VEG..... ..........    250

E1 Cat Domain    GGNLQGAGQY PVVLNVFNRL VYSAELYATS VYFDLWESDP TENHDEHGLW    263
GUN_BACPO        GGNLTGVANY PVVLDVINRV VYSFHLYGPG VSSQPWNDP APFHNLHAIW    298
GUNA_XANCP_CAT   GGNLQPLACT PLNI-PANRL LLAHRMYGPD VFVQSYFNDS NFPNMPAIW    261
Consensus        GGNL...... P..... NR. ....... MY.... V......... ...N.P.IW    300

E1 Cat Domain    NKNWGYLFNQ NIAPVWLGEF GTTLQSTTDQ TWLKTLVQYL RPTAQYGADS    313
GUN_BACPO        DQTWGYISKQ NIAPVLVGEF GGRNVDLSSP E--GKWQNAL VHYIG-ANNL    345
GUNA_XANCP_CAT   ERHFGQFA-- GTHALLIGEF GGKYGEGDAR D--KTWQIAL VKYLR-SKGI    306
Consensus        ....G..... ........EF G.......... ......Q.AL ........... 350

E1 Cat Domain    FQWTLWSWNP NSGDTGGILK DDWQTVDTVK DGYLAPIKSS IF----DPVG    359
GUN_BACPO        YFT-YWSLNP NSGDTGGILL DDWITWNREK QDMLGRIMKP VVSVAQQAEA    394
GUNA_XANCP_CAT   NQGFYWSWNP NSGDTGGILR DDWISVRQDK MTILRTLW-- --------GT    346
Consensus        ....YWS.NP NSGDTGG.L. DDW........ ......... ........... 400

E1 Cat Domain    ASA                                                     362
GUN_BACPO        AAE                                                     397
GUNA_XANCP_CAT   AGN                                                     349
Consensus        A..                                                     403
```

FIG. 6

GENE CODING FOR THE E1 ENDOGLUCANASE

The United States Government has rights in this invention under Contract No. DE-AC02-83CH10093 between the United States Department of Energy and the National Renewable Energy Laboratory, a Division of the Midwest Research Institute.

This application is a continuation-in-part of Ser. No. 08/125,115 filed Sep. 21, 1993, now U.S. Pat. No. 5,366,884, which is a continuation-in-part of 07/826,089 filed Jan. 27, 1992, now U.S. Pat. No. 5,275,944, which was a continuation-in-part of Ser. No. 412,434 filed Sep. 26, 1989 now U.S. Pat. No. 5,110,735.

FIELD OF THE INVENTION

The invention relates to genes encoding *Acidothermus cellulolyticus* E1 endoglucanase, recombinant microorganisms containing the gene and their use to express the gene to produce the enzyme or to degrade cellulose.

BACKGROUND OF THE INVENTION

The fermentable fractions of biomass include cellulose (β-1,4-linked glucose) and hemicellulose. Cellulose consists of long, covalently bonded insoluble chains of glucose which are resistant to depolymerization. Hemicellulose is a heterogeneous fraction of biomass that is composed of xylose and minor five- and six-carbon sugars. Although it is an abundant biopolymer, cellulose is highly crystalline, insoluble in water, and highly resistant to depolymerization. The complete enzymatic degradation of cellulose to glucose, probably the most desirable fermentation feedstock, may be accomplished by the synergistic action of three distinct classes of enzymes. The first class, the "endo-β-1,4-glucanases" or β-1,4-D-glucan 4-glucanohydrolases (EC 3.2.1.4), acts at random on soluble and insoluble β-1,4-glucan substrates to brake the chains and are commonly measured by the detection of reducing groups released from carboxymethylcellulose (CMC). The second class, the "exo-β- 1,4-glucosidases", includes both the β-1,4-D-glucan glucohydrolases (EC 3.2.1.74), which liberate D-glucose from 1,4-β-D-glucans and hydrolyse cellobiose slowly, and β-1,4-D-glucan cellobiohydrolase (EC 3.2.1.91) which liberate D-cellobiose from β-1,4-glucans. The third class, the "β-D-glucosidases" or β-D-glucoside glucohydrolases (EC 3.2.1.21), act to release D-glucose units from soluble cellodextrins, especially cellobiose, and an array of aryl-glycosides.

The development of an economic process for the conversion of low-value biomass to ethanol via fermentation requires the optimization of several key steps, especially that of cellulase production. Practical utilization of cellulose by hydrolysis with cellulase to produce glucose requires large amounts of cellulase to fully depolymerize cellulose. For example, about one kilogram cellulase preparation may be used to fully digest fifty kilograms of cellulose. Economical production of cellulase is also compounded by the relatively slow growth rates of cellulase producing fungi and the long times required for cellulase induction. Therefore, improvements in or alternative cellulase production systems capable of greater productivities, higher specific activities of cellulase activity or faster growth rates than may be possible with natural fungi would significantly reduce the cost of cellulose hydrolysis and make the large-scale bioconversion of cellulosic biomass to ethanol more economical.

Highly thermostable cellulase enzymes are secreted by the cellulolytic thermophile *Acidothermus cellulolyticus* gen. nov., sp. nov. These are discussed in U.S. Pat. Nos. 5,275,944 and 5,110,735. This bacterium was originally isolated from decaying wood in an acidic, thermal pool at Yellowstone National Park and deposited with the American Type Culture Collection (ATCC) under collection number 43068 (Mohagheghi et al. 1986. *Int. J. System. Bacteriol.* 36:435–443).

The cellulase complex produced by this organism is known to contain several different cellulase enzymes with maximal activities at temperatures of 75° C. to 83° C. These cellulases are resistant to inhibition from cellobiose, an end product of the reactions catalyzed by cellulase. Also, the cellulases from *Acidothermus cellulolyticus* are active over a broad pH range centered about pH 6, and are still quite active a pH 5, the pH at which yeasts are capable of fermenting glucose to ethanol. A high molecular weight cellulase isolated from growth broths of *Acidothermus cellulolyticus* was found to have a molecular weight of approximately 156,600 to 203,400 daltons by SDS-PAGE. This enzyme is described by U.S. Pat. No. 5,110,735.

A novel cellulase enzyme, known as the E1 endoglucanase, also secreted by *Acidothermus cellulolyticus* into the growth medium, is described in detail in U.S. Pat. No. 5,275,944. This endoglucanase demonstrates a temperature optimum of 83° C. and a specific activity of 40 μmole glucose release from carboxymethylcellulose/min/mg protein. This E1 endoglucanase was further identified as having an isoelectric pH of 6.7 and a molecular weight of 81,000 daltons by sodium dodecyl sulfate polyacrylamide gel electrophoresis.

It has been proposed to use recombinant cellulase enzymes to either augment or replace costly fungal enzymes for cellulose degradation (Lejeune, Colson, and Eveleigh, In *Biosynthesis and Biodegradation of Cellulose,* C. Haigler and P. J. Weimer, Eds., Marcel-Dekker, New York, N.Y. 1991, pp. 623–672). The genes coding for *Acidothermus cellulolyticus* cellulases cloned into *Streptomyces lividans, E. coli,* Bacillus, or other microbial host organisms could provide an abundant, inexpensive source of highly active enzymes. However, in order to produce recombinant E1 endoglucanase, the gene encoding this enzyme must be available and well characterized.

SUMMARY OF THE INVENTION

It is an object of the present invention to clone the gene for the E1 endoglucanase from *Acidothermus cellulolyticus.*

It is another object of the present invention to transform and express this E1 endonuclease gene in a different microbial host under the same and/or a different gene regulatory system.

It is a further object of the present invention to prepare mutant E1 endoglucanases which have different properties from the natural enzyme.

It is another further object of the present invention to prepare hybrid endoglucanases, one part of which corresponds to a portion of the sequence of the E1 endoglucanases or its mutants.

It is yet another object of the present invention to hydrolyse cellulose in cellulosic materials by contacting the cellulosic material with the E1 endoglucanases produced by expression of the native or altered E1 gene.

The present invention describes the gene for and the nucleotide sequence of the segment of *Acidothermus cellu-*

*lolyticus* DNA encoding the E1 endoglucanase gene. This 3004 base fragment of DNA is unique in nature and discretely defined. The natural gene contains a ribosome binding site followed by three direct repeats of an 8 base sequence of unknown function, signal peptide, open reading frame, termination codon, a putative transcriptional terminator, and a putative transcriptional regulatory sequence which shows homology to sequences found upstream of cellulase genes isolated from other actinomycete bacteria.

The cloned gene may be expressed in other microorganisms under its natural promotor or another promotor recognized by the host microorganism. Alternatively, additional copies of the gene may be introduced into *Acidothermus cellulolyticus* to enhance expression of the enzyme. Additionally, DNA encoding one or more domains or fragments of the *Acidothermus cellulolyticus* E1 endoglucanase may be ligated to domains or fragments from other compatible endoglucanases to create a novel recombinant DNA capable of expressing a hybrid endoglucanase enzyme having beneficial properties from both endoglucanases or any portion thereof.

BRIEF DESCRIPTION OF THE DRAWINGS

FIG. 1 shows the 3004 base pair nucleotide sequence of the region of *Acidothermus cellulolyticus* genomic DNA which contains the E1 endoglucanase gene.

FIG. 2 shows the amino acid translation of the coding sequence described in FIG. 1.

FIG. 6 shows an amino acid sequence comparison between the catalytic domains of two homologous endoglucanases from different bacteria, *Bacillus polymyxa* B-1,4-endoglucanase (GUN_BACPO) Swiss-Prot. Accession # P23548, *Xanthomonas campestis* B-1,'4-endoglucanase A (GUNA_XANPC_CAT) Swiss-Prot. Accession # P19487, *Acidothermus cellulolyticus* E1 endoglucanase (E1 cat domain) and a consensus sequence.

DESCRIPTION OF THE PREFERRED EMBODIMENTS

According to the present invention the gene for *Acidothermus cellulolyticus* E1 endoglucanase is cloned and expressed in a different microbial host. This enzyme is a β-1-4 endoglucanase or endocellulase which can hydrolyze cellulose preferably and xylan to some degree and is hereafter referred to as E1 endoglucanase. The result is a vastly improved rate of enzyme production, thereby lowering the cost of cellulase and the production of alcohol using cellulosic materials as substrates.

While endoglucanase alone is generally insufficient to completely hydrolyze cellulose, the enzyme product of the present invention may be used alone or preferably in combination with other cellulases to improve overall effectiveness.

Figure 3:
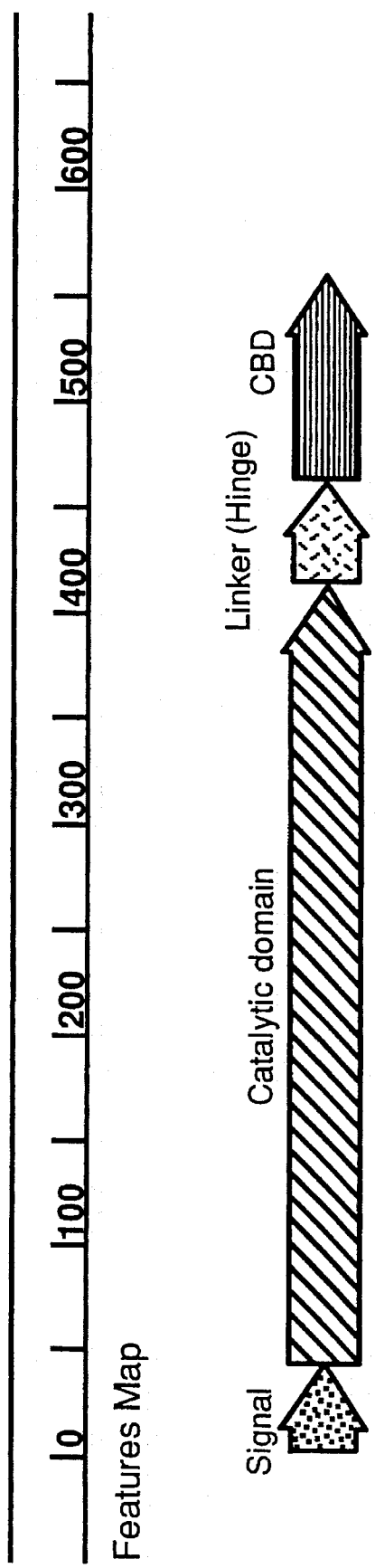
FIG. 3 shows a schematic illustration of the suspected domain architecture of the *Acidothermus cellulolyticus* E1 endoglucanase protein. This Figure includes the relative locations of the catalytic, linker, and cellulose binding domains aligned with the amino acid residues numbered 1–562 from the N-terminus.
Figure 4:
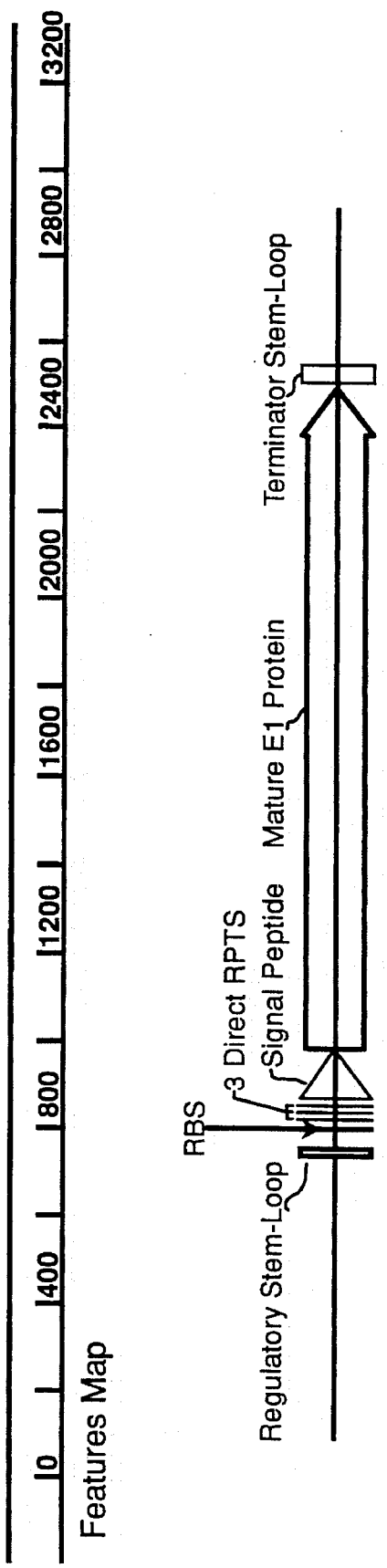
FIG. 4 shows a schematic illustration of the putative transcriptional and translational regulatory sequences associated with the E1 endoglucanase gene aligned with the nucleotide sequence coordinates of the E1 gene.

The coding portion of the gene appears to be 1686 base pairs long corresponding to 562 amino acids. The mature protein has an N-terminal amino acid sequence which commences at residue 42 and is 521 amino acids in length. Presumably the first 41 amino acids encode a signal sequence which is cleaved to yield the active E1 endoglucanase enzyme. The nucleotide and amino acid sequences may be seen in FIGS. 1 and 2, respectively. Review of the amino acid sequence deduced from the gene sequence indicates that the protein is architecturally similar to other cellulase genes. It is a multi-domain protein, comprising a catalytic domain, a linker region and a cellulose binding domain of very characteristic amino acid sequence. The approximate gene architecture is shown in FIGS. 3 and 4.

The *Acidothermus cellulolyticus* E1 endoglucanase gene was cloned using standard recombinant DNA techniques as will be described below. Variations on these techniques are well known and may be used to reproduce the invention. Alternatively, the DNA molecule of the present invention can be produced through any of a variety of other means, preferably by application of recombinant DNA techniques, the polymerase chain reaction techniques (PCR) or DNA synthesis of the gene. Techniques for synthesizing such molecules are disclosed by, for example, Wu et al, *Prog. Nucl. Acid. Res. Molec. Biol.* 21:101–141 (1978).

Standard reference works setting forth the general principles of recombinant DNA technology and cell biology include Watson et al., *Molecular Biology of the Gene*, Volumes I and II, Benjamin/Cummings Publishing Co., Inc., Menlo Park, Calif. (1987); Darnell et al., *Molecular Cell Biology*, Scientific American Books, Inc., New York, N.Y. (1986); Lewin, *Genes II*, John Wiley & Sons, New York, N.Y. (1985); Old et al., *Principles of Gene Manipulation: An Introduction to Genetic Engineering*, 2nd Ed., University of California Press, Berkeley, Calif. (1981); Sambrook et al, (*Molecular Cloning: A Laboratory Manual*, 2nd Edition, Cold Spring Harbor Press, Cold Spring Harbor, N.Y. (1989)) and Albers et al., *Molecular Biology of the Cell*, 2nd Ed., Garland Publishing, Inc., New York, N.Y. (1989).

Procedures for constructing recombinant molecules in accordance with the above-described method are disclosed by Sambrook et al., supra. Briefly, a DNA sequence encoding the endoglucanase gene of the present invention, or its functional derivatives, may be recombined with vector DNA in accordance with conventional techniques, including blunt-ended or cohesive termini for ligation, restriction enzyme digestion to provide appropriate termini, filling in of cohesive ends as appropriate, alkaline phosphatase treatment to avoid undesirable joining, ligation with appropriate ligases. Part or all of the genes may be synthesized chemically in overlapping fragments which are hybridized in groups and ligated to form longer double-stranded DNA molecules. The resulting vector may then be introduced into a host cell by transformation, transfection, electroporation, etc. Techniques for introducing a vector into a host cell are well known.

A vector is a DNA molecule, derived from a plasmid, bacteriophage or hybrid, into which fragments of DNA may be inserted or cloned. A vector will contain one or more unique restriction sites, and may be capable of autonomous replication or integration into the genome of a defined host or vehicle organism such that the cloned sequence is reproducible.

Another embodiment of the present invention relates specifically to the native 3004 nucleotide sequence of DNA encoding the *Acidothermus cellulolyticus* E1 endoglucanase enzyme and accompanying flanking sequences. This DNA encodes a 562 amino acid sequence which is shown in FIG. 2. The molecular weight of the protein deduced from the amino acid sequence is 60648 daltons and includes a putative 41 amino acid signal peptide. Other DNA sequences encoding the same 562 amino acids may readily be used as several amino acids are coded for by a plurality of different DNA triplet codons. Therefore, the gene encoding the *Acidothermus cellulolyticus* E1 endoglucanase may be any DNA which encodes that amino acid sequence. The mature E1 protein is comprised of 521 amino acids with a predicted molecular weight of 56415 daltons.

One may also use an expression vector as the vehicle to clone the E1 endoglucanase gene. In such a situation, the host cell will direct expression of the cloned E1 endoglucanase coding sequence using a promotor sequence which turns expression on or off under defined conditions. The protein may be separated, purified and assayed, or assayed directly from crude host cell homogenates or culture medium.

An expression vector is any DNA element capable of replicating in a host cell independently of the host's chromosome, and which can control the expression of a coding sequence inserted into it at specific locations and in a particular orientation. Such DNA expression vectors include bacterial plasmids and phages and typically include promoter sequences to facilitate gene transcription.

In the situation where the E1 endoglucanase gene of the present invention has been cloned in a vector and expression has not occurred, the gene may be removed from the vector and inserted into an expression vector suitable for expressing the gene.

The DNA is said to be capable of expressing a polypeptide if it contains nucleotide sequences which contain signals for transcriptional and translational initiation, and such sequences are operably linked to nucleotide sequences which encode the polypeptide. An operable linkage is a linkage in which the signals for transcriptional and translational initiation and the DNA sequence sought to be expressed are connected in such a way as to permit gene expression. The precise nature of the signals required for gene expression vary from organism to organism.

The native promotor for *Acidothermus cellulolyticus* E1 endoglucanase may not be functional or efficient for expression in certain microbial hosts. In such a situation, a suitable promotor region of DNA may be ligated upstream from the E1 endoglucanase coding sequence to control its expression. In addition to the promotor, one may include regulatory sequences to modulate the level and/or timing of gene expression. Expression may be controlled by an inducer or a repressor so that the recipient microorganism expresses the gene(s) only when desired.

A promoter (e.g. transcriptional regulatory region) directs the precise location in the gene and the relative strength of initiation of RNA transcription. Downstream DNA sequences, when transcribed into RNA, will signal the initiation of protein synthesis by the incorporation of a ribosome binding sequence. Regions will normally include those 5'-non-coding sequences involved with initiation of transcription and translation, such as the −10 to −35 sequences ribosome binding site, and the like. Other sequences which influence gene expression are also considered regulatory sequences. In practice, the distinction may be blurred as the two regions may overlap each other. These sequences may be either the natural sequences from the *Acidothermus cellulolyticus* E1 endoglucanase gene, they may be taken from other genes, be synthetic or a combination of these.

If desired, the non-coding region 3' to the gene sequence coding for E1 endoglucanase may be obtained by the above-described methods. This region may be utilized for its transcriptional termination regulatory sequences. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted. Transcriptional terminators are characterized by large inverted repeat sequences, which can form extensive step-loop secondary structures in DNA or RNA.

For expressing the E1 endoglucanase gene, one may use a variety of microbial hosts including most bacteria, yeast, fungi and algae. Organisms which are capable of secreting large amounts of protein into the external environment would make ideal hosts for cellulase gene expression.

If the host cell is a bacterium, generally a bacterial promoter and regulatory system will be used. For a typical bacterium such as *E. coli*, representative examples of well known promoters include trc, lac, tac, trp, bacteriophage lambda $P_L$, T7 RNA polymerase promoter, etc. When the expression system is yeast, examples of well known promoters include: GAL 1/GAL 10, alcohol dehydrogenase (ADH), his3, cycI, etc. For eukaryotic hosts, enhancers such as the yeast Ty enhancer, may be used.

Alternatively, if one wished for the E1 endoglucanase gene to be expressed only at a particular time, such as after the culture or host organism has reached maturity, an externally regulated promoter is particularly useful. Examples include those based upon the nutritional content of the medium (e.g. lac, trp, his), temperature regulation (e.g. temperature sensitive regulatory elements), heat shock promoters (e.g. HSP80A, U.S. Pat. No. 5,187,267), stress response (e.g. plant EF1A promoter, U.S. Pat. No. 5,177,011) and chemically inducible promoters (e.g. tetracycline inducible promoter or salicylate inducible promoter U.S. Pat. No. 5,057,422).

Other suitable hosts for expressing E1 endoglucanase include Trichoderma, Fusarium, Penicillium, Bacillus, Xanthomonas, Zymomonas. These microorganisms may also serve as sources of endoglucanase genes for the formation of mixed domain genes for the production of hybrid enzymes.

Expression of the native E1 endoglucanase gene has been demonstrated in both *E. coli* and in *Streptomyces lividans*. Expressing E1 endoglucanase in *E. coli* has also been performed under control of a T7 bacteriophage promoter, and could be accomplished using other promoters recognizable by *E. coli*. Expression in *E. coli* has been enhanced by at least a factor of five relative to the native gene with the constructs of the present invention. Expression of the E1 endoglucanase coding sequence under control of the tipA promoter (thiostrepton-inducible) in *S. lividans* has also been accomplished.

Intact native, variant or hybrid E1 endoglucanase proteins can be efficiently synthesized in bacteria by providing a strong promoter and an acceptable ribosome binding site. To express a prokaryotic gene that has an acceptable natural ribosome binding site, only a promoter must be supplied. Levels of expression may vary from less than 1% to more than 30% of total cell protein.

Chemical derivatives of the E1 endoglucanase DNA or the E1 endoglucanase protein are also included within the definition of that DNA or protein. Examples of chemical derivatives include but are not limited to: labels attached to the molecule, chemically linking the molecule to an additional substance, methylation, acylation, thiolation, chemical modification of a base or amino acid, etc.

The nucleotide sequence may be altered to optimize the sequence for a given host. Different organisms have different codon preferences as has been reported previously. Codon usage may affect expression levels in host organisms. Furthermore, the nucleotide sequence may be altered to provide the preferred three dimensional configuration of the mRNA produced to enhance messenger RNA stability, ribosome binding and expression. Alternatively, the change can be made to enhance production of active enzyme, such as changing internal amino acids to permit cleavage of E1 endoglucanase from a fusion peptide or to add or subtract a site for various proteases. Oike, Y., et al., *J. Biol. Chem.* 257: 9751–9758 (1982); Liu, C., et al., *Int. J. Pept. Protein Res.* 21: 209–215 (1983). It should be noted that separation of E1 endoglucanase from a leader sequence is not necessary provided that the E1 endoglucanase activity is sufficiently acceptable.

Changes to the sequence such as insertions, deletions and site specific mutations can be made by random chemical or radiation induced mutagenesis, restriction endonuclease cleavage to create deletions and insertions, transposon or viral insertion, oligonucleotide-directed site specific mutagenesis, or by such standard site specific mutagenesis techniques as Botstein et al, *Science* 229: 193–210 (1985).

Such changes may be made in the present invention in order to alter the enzymatic activity, render the enzyme more susceptible or resistant to temperature, pH, or chemicals, alter regulation of the E1 endoglucanase gene, alter the mRNA or protein stability (half-life) and to optimize the gene expression for any given host. These changes may be the result of either random changes or changes to a particular portion of the E1 endoglucanase molecule believed to be involved with a particular function. To further enhance expression, the final host organism may be mutated so that it will change gene regulation or its production of the E1 endoglucanase gene product.

Such alterations in either the nucleotide sequence or the amino acid sequences are considered variants of the natural sequences. Nucleotide sequence changes may be conservative and not alter the amino acid sequence. Such changes would be performed to change the gene expression or ability to easily manipulate the gene. Nucleotide sequence changes resulting in amino acid substitutions, insertions or deletions are generally for altering the enzyme product to impart different biological properties, enhance expression or secretion or for simplifying purification. Changes in the DNA sequence outside the coding region may also be made to enhance expression of the gene or to improve the ease of DNA manipulation.

The natural amino acid sequence is believed to contain a signal region and three domains corresponding as follows:

| Key    | From | To  | Description                            |
|--------|------|-----|----------------------------------------|
| SIGNAL | 1    | 41  | Putative signal peptide                |
| SIGNAL | 14   | 41  | Putative signal peptide (alternative)  |
| DOMAIN | 42   | 404 | Catalytic domain                       |
| DOMAIN | 405  | 460 | Linker                                 |
| DOMAIN | 461  | 562 | CBD                                    |

The N-terminal amino acid sequence determined from native purified E1 endoglucanase corresponds to amino acids 42 to 79 (FIG. 2). Thus the mature N-terminus of the E1 endoglucanase begins at residue 42.

While the term "variants" generally does not encompass large changes in the amino acid sequence, in the present application, the term "variants" includes a large number of changes outside the catalytic region of the endoglucanase. For example, a significant deletion of the native gene as described in Example 4 below. Other large deletions outside the catalytic region such as in the signal, hinge, CBD domains or portions of the catalytic domain are also readily apparent and would be considered "variants".

For the purposes of this application, the terms "hybrid enzyme" or "hybrid protein" includes all proteins having at least one functional domain or fragment originating substantially from one protein and another functional domain or fragment substantially originating from at least one different protein. The domains may also be spliced together internally and fragments may be used which by themselves may not be complete functional domains. Signal sequences may be considered domains.

Hybrid enzymes of E1 endoglucanase may be prepared by ligating DNA encoding one or more E1 endoglucanase domains to one or more domains from one or more different cellulase genes. Representative examples of other cellulase genes which may be used are *Bacillus polymyxa* β-1,4-endoglucanase (Baird et al, *Journal of Bacteriology*, 172:1576–86 (1992)) and *Xanthomonas campestis* β-1,4-endoglucanase A (Gough et al, *Gene* 89:53–59 (1990)). The number of domains in the hybrid protein may be the same or different from any natural enzyme. A large number of different combinations are possible, as a large number of cellulases have now been cloned and sequenced.

It is further contemplated that more than one catalytic domain may be included in the hybrid enzyme. This may result in an increased specific activity and/or altered functionality. Also, a catalytic domain containing cellulase activity other than endonuclease activity may be included as well to reduce the number of cellulase enzymes one needs to add to a cellulosic substrate for polymer degradation.

Another preferred embodiment is to use the E1 endoglucanase produced by recombinant cells to hydrolyse cellulose in cellulosic materials for the production of sugars per se or for fermentation to alcohol or other chemicals, single cell protein, etc. The processes for the fermentation of sugars to alcohol and its many variations are well known.

In situations where it is desired to simultaneously ferment the sugars produced by hydrolysis of cellulose, one may use yeast or Zymomonas as suitable hosts for introducing the E1 endoglucanase gene or use a mixed culture of an alcohol producing microbe and the E1 endoglucanase enzyme or microbe producing enzyme. If insufficient endoglucanase protein is released, the culture conditions may be changed to enhance release of enzyme. Other suitable hosts include any microorganism fermenting glucose to ethanol such as Lactobacillus or Clostridium and microorganisms fermenting a pentose to ethanol.

Either yeast or Zymomonas may be employed as a recombinant host for cellulase gene expression. However, yeast (*Saccharomyces cerevisiae*) is known to be a poor host for proteins when secretion into the medium is desired. At the present time, the capacity of Zymomonas to secrete large amounts of proteins is not understood thoroughly. However, heterologous cellulase genes have been transferred into and expressed at fairly low levels in both *S. cerevisiae* (Bailey et al., Biotechnol. Appl. Biochem. 17:65–76, (1993) and in Zymomonas (Su et al., Biotech. Lett. 15:979–984, (1993) as well as in other bacterial and fungal species.

For industrial uses, cellulase enzymes that display thermal stability, such as E1 endoglucanase, generally have enhanced stability under harsh process conditions as well as high temperatures. Since shear forces are applied during pumping and stirring, additional stability from this stress is desired. Other benefits include resistance to pH changes, a potential advantage with residual acid remaining from acid pretreatment of cellulosic materials, and resistance to proteases which are produced by common microbial contaminants.

Even if the genes for E1 endoglucanase are not secreted, considerable amounts of cell death and cell lysis occurs during processing due to shearing and pressure differences, thereby releasing some of the enzyme into the surrounding medium. Leakage of enzyme may be enhanced by a number of culture conditions which increase cell membrane permeability such as temperature and osmotic changes, surfactants, lytic agents (proteases, antibiotics, bacteriophage infection, etc.) and physical stress.

Unless specifically defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

EXAMPLE 1

Genome Library Construction, Library Screening, and Subcloning

Genomic DNA was isolated from *Acidothermus cellulolyticus* and purified by banding on cesium chloride gradients. Genomic DNA was partially digested with Sau 3A and separated on agarose gels. DNA fragments in the range of 9–20 kilobase pairs were isolated from the gels. This purified Sau 3A digested genomic DNA was ligated into the Bam H1 acceptor site of purified EMBL3 lambda phage arms (Clontech, San Diego, Calif.). Phage DNA was packaged according to the manufacturer's specifications and plated with *E. coli* LE392 in top agar which contained the soluble cellulose analog, carboxymethylcellulose (CMC). The plates were incubated overnight (12–24 hours) to allow transfection, bacterial growth, and plaque formation. Plates were stained with Congo Red followed by destaining with 1 M NaCl. Lambda plaques harboring endoglucanase clones showed up as unstained plaques on a red background.

Lambda clones which screened positive on CMC-Congo Red plates were purified by successive rounds of picking, plating and screening. Individual phage isolates were named SL-1, SL-2, SL-3 and SL-4. Subsequent subcloning efforts employed the SL-2 clone which contained an approximately 13.7 kb fragment of *A. cellulolyticus* genomic DNA.

Standard methods for subcloning DNA fragments can be found in *Molecular Cloning A Laboratory Manual* (J. Sambrook, E. F. Fritsch and T. Maniatis, Cold Spring Harbor Laboratory Press, second edition, 1989). Purified SL-2 insert DNA was cut with BamH1, Pvu1 and EcoR1. Resulting fragments of DNA were individually purified by electrophoretic separation on agarose gels. BamH1 digestion yielded two fragments derived from gene SL-2 insert DNA, 2.3 and 9 kb in length. Pvu1 digestion yielded fragments of 0.7, 0.9, 1.7, 2.4, 3.3, and 3.7 kb. EcoR1 digestion produced insert-derived fragments of 0.2, 0.3, 1.9, 2.4 and 3.7 kb in length. Individual purified restriction fragments were ligated into plasmid vectors previously cut with the appropriate restriction enzyme. Specifically, the 2.3 and the 9 kb BamH1 fragments were ligated separately into BamH1 cut pBR322 and pGEM7. Pvu1 fragments were ligated separately into Pvu1 cut pBR322. The 3.7 kb Pvu1 fragment was also blunt ended by treatment with T4 DNA polymerase and ligated into the SmaI site of pGEM7. EcoR1 fragments were ligated into EcoR1 cut pBR322.

Ligation products were transformed into competent *E. coli* DH5α cells and plated onto appropriate selective media (LB+15 µg/ml tetracycline or LB+50 µg/ml ampicillin) containing 1 mM of the substrate analog, 4-methylumbelliferyl-cellobioside (4-MUC), and grown overnight at 37° C. Cleavage of the 4-MUC by β-1,4-endoglucanase activity results in the formation of a highly fluorescent aglycone product, 4-methylumbelliferone. Plates were inspected for fluorescing colonies under long wave ultraviolet light to determine which subclones harbor fragments of *A. cellulolyticus* DNA encoding functional cellulase genes. Plasmids were purified from fluorescing colonies and the size of the subcloned DNA verified by restriction digestion. By these methods it was possible to determine that the 2.3 kb BamH1 fragment encodes a cellulase activity, as does the 3.7 kb Pvu1 fragment. It has been shown by Southern blot hybridization experiments that the 2.3 kb BamH1 fragment and the 3.7 kb Pvu1 fragment contain homologous DNA sequences. DNA sequencing was performed with templates containing *A. cellulolyticus* DNA inserted into the plasmid pGEM7.

| Subclone name | Description |
|---|---|
| p52 | 2.3 kb BamH1 fragment from λSL-2 in BamH1 site of pGEM7 |
| p53 | 2.3 kb BamH1 fragment from λSL-2 in BamH1 site of pGEM7 (opposite orientation) |
| 4-5 | 3.7 kb Pvu1 fragment from λSL-2 in Sma1 site of pGEM7 |
| 4-9 | 3.7 kb Pvu1 fragment from λSL-2 in Sma1 site of pGEM7 (opposite orientation) |

A 2.3 kb Bam H1 fragment and an overlapping 3.7 kb Pvu1 fragment from λSL-2 were shown to express CMCase activity.

Bi-directional Deletion Subclones for Sequencing

Bi-directional deletion subclones of the 2.3 kb Bam H1 subclone from SL-2 were produced using the commercially available Exo III/Mung bean nuclease deletion kit from Promega. A 2.3 kb BamH1 fragment isolated from clone SL-2 was cloned in both orientations into the BamH1 site of an *E. coli* vector called pGEM-7Zf(+) (Promega Corp., Madison, Wis.). These clones are referred to as p52 and p53, respectively. Two sets of nested deletion clones were produced according to the manufacturer's specifications using the Erase-a-Base® deletion system available from Promega. Deletions were constructed by double digesting the plasmid with HindIII and Kpnl. The 5' overhanging sequences resulting from HindIII cleavage provide a starting point for ExoIII deletion. The 3' overhanging sequences resulting from cleavage by Kpnl protect the vector DNA from ExoIII digestion. Thus, deletions are unidirectional from the HindIII site, not bi-directional.

Double digested plasmid DNA was then exposed to digestion by the 3' to 5' exodeoxyribonuclease, ExoIII, and aliquots of the reaction were removed at various time points into a buffer which halts ExoIII activity. S1 nuclease, a single strand specific endonuclease, was then added to remove single stranded DNA and to blunt end both ends of the deletion products. T4 DNA ligase was then used to re-circularize plasmid DNAs and the products were transformed into competent *E. coli* cells.

A representative sampling of the resulting clones are screened by restriction enzyme analysis of plasmid DNAs in order to estimate the extent of deletion. Deletions endpoints occurred fairly randomly along the sequence and clones were selected for sequencing such that deletion endpoints are spaced at approximately 100 to 300 bp intervals from either end of the 2.3 kb BamH1 fragment. One set of clones is a succession of progressively longer deletions from one end of clone p52 and the other is a similar set of successively longer deletions from p53. Please refer to FIG. 5 for the appropriate length of each deletion mutant. Each of the deletion clones was plated on MUC indicator plates to determine which still exhibited endoglucanase activity. Retention of β-1,4-glucanase activity in the deletion subclones is indicated by the symbol, "+"; lack of activity by the symbol, "−", after the name of each clone listed in FIG. 5.

Manual DNA Sequencing

Figure 5:
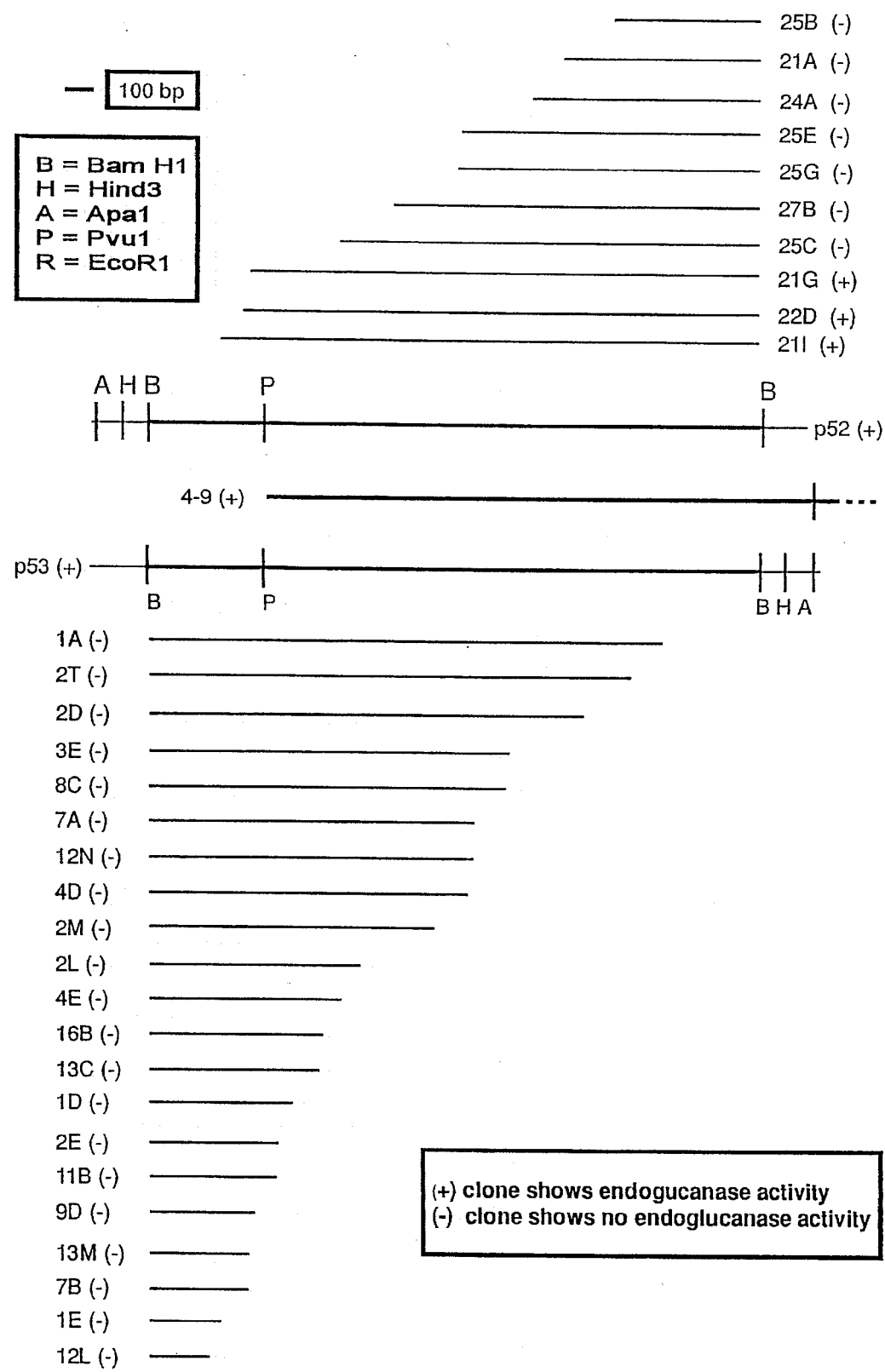
FIG. 5 shows the regions remaining in many deletion mutants of the original E1 gene clone and whether or not the remaining gene fragment expresses a protein with endoglucanase activity.

Sequencing reactions were performed using double-stranded plasmid DNAs as templates. Templates used for DNA sequencing reactions included each of the plasmid DNAs diagrammed in FIG. 5. In order to complete the sequencing of the E1 gene another subclone was employed as a template in conjunction with synthetic oligonucleotides used as primers. The 3.7 kb Pvu1 fragment from SL-2 was blunt ended with T4 DNA polymerase and cloned in both orientations into the SmaI site of pGEM7, resulting in clones 4–5 and 4–9. The 3.7 kb Pvu1 fragment largely overlaps the 2.3 kb BamH1 subclone (as shown in FIG. 5). Newly synthesized oligonucleotide primers were used to sequence the 810 base pairs downstream of the internal BamH1 located at position 2288 of the DNA sequence.

The reactions were carried out using alpha-$^{35}$S-dATP to label DNA synthesized using the T7 DNA polymerase kit provided by United States Biochemicals. Reaction products were separated on wedge acrylamide gels and were autoradiographed after fixation and drying. X-ray films were read using the gel reader apparatus (a model GP7 MarkII sonic digitizer, manufactured by Science Accessories Corp., Stratford, Conn.) and GeneWorks™ software package provided by Intelligenetics, Inc. (Mountain View, Calif.). Sequences were checked and assembled using the same software package.

EXAMPLE 2

Analysis of the Gene Coding for E1 Endoglucanase

Three peptide sequences have been obtained from purified endoglucanase E1 from *Acidothermus cellulolyticus*. Thirty-eight amino acids have been determined from the N-terminus of the E1 protein by automated Edman degradation. The 38 amino acid sequence is identical to the previously determined (U.S. Pat. No. 5,275,944) 24 N-terminal amino acids and extends that N-terminal sequence of the native protein by another 14 amino acids. The N-terminal sequences are as follows:

AGGGYWHTSG REILDANNVP VRIA
(reported in U.S. Pat. #5,275,944), (SEQ ID NO:2)

AGGGYWHTSG REILDANNVP VRIAGINWFG FETXNYVV
(this work), (SEQ ID NO:2)

Figure 1:
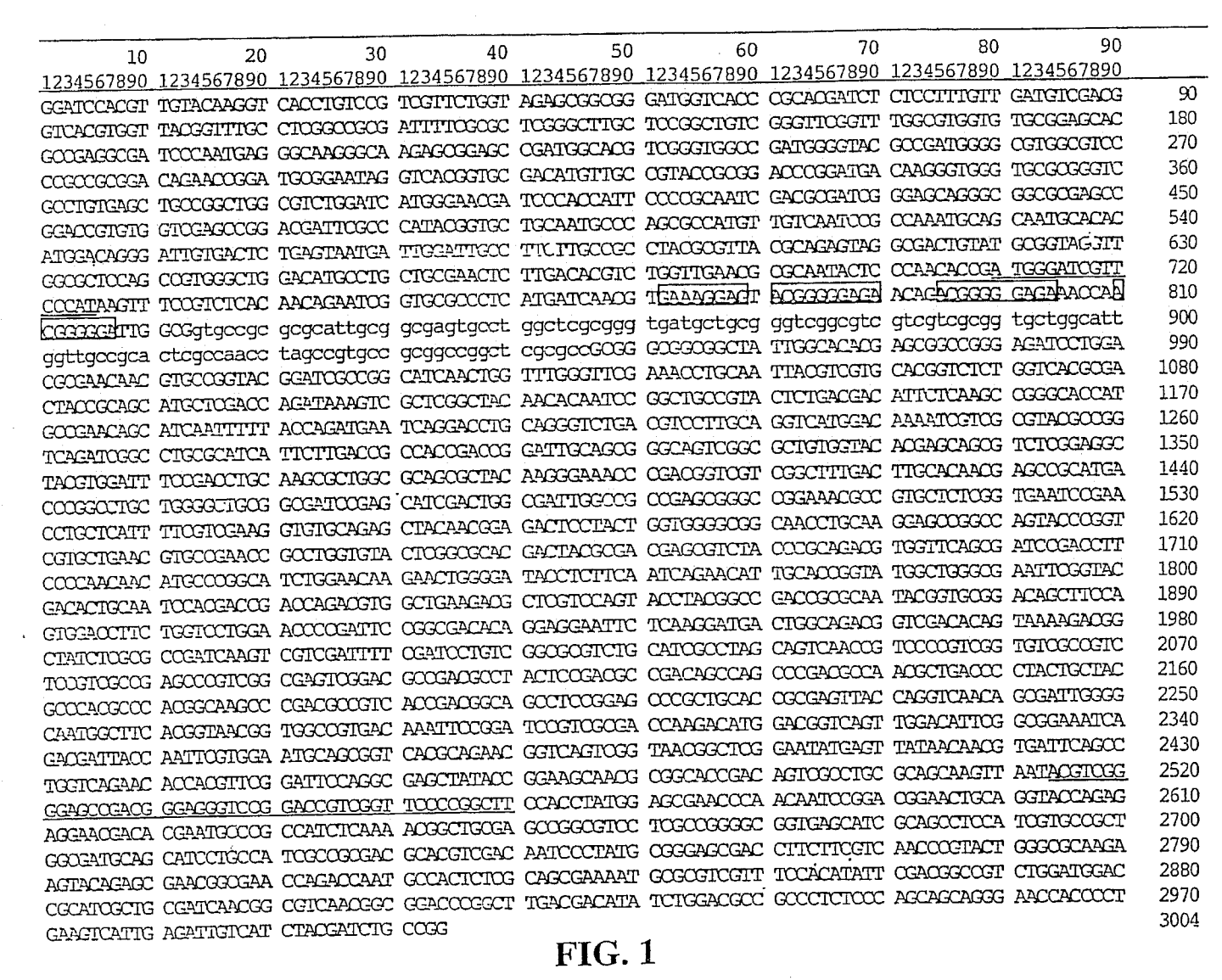

A comparison of the translation of the nucleotide sequence data in FIG. 1 and the peptide sequences available from purified E1 endoglucanase indicates that this clone encodes the E1 endoglucanase protein. The N-terminal 38 amino acid sequence is in exact agreement with the translation of the DNA sequence between nucleotides 947–1060 in FIG. 1. This long sequence of 38 amino acids was not found in any other entry in the Swiss-Prot database (version 28).

EXAMPLE 3

Gene Architecture

While not wishing to be bound by any particular theory, the following hypothesis is presented. FIG. 1 shows that the mature translation product beginning with a GCG codon at position 947–949 and extends to a TAA terminator codon at position 2410–2412. Since cellulases are secreted, presumably to gain access to their substrates, one may assume a signal peptide is present which assists in the secretion process in vivo. A nucleotide sequence apparently comprising the signal peptide for the E1 endoglucanase is encoded by the nucleotide sequence from 824–946. This stretch of 123 base pairs encodes 41 amino acids, beginning with a GTG (valine) codon. We postulate that the translation start site is the GTG codon at position 824–826 instead of the more usual ATG (methionine) codon (position 863–865) because of the proximity of the GTG start codon to a putative upstream ribosome binding sites (RBS), and because of the better amino-terminal charge density on the longer signal peptide. Alternatively, the signal sequence may start with the methionine at position 14 of the apparent signal. For the purposes of gene manipulations, either signal sequence may be used.

The putative RBS for the E1 endoglucanase gene is pointed out by the excellent homology (8 of 9 residues) to the published 3' end of the *S. lividans* 16S rRNA at positions 772–779 (Bibb and Cohen, 1982, *Mol. Gen. Genet.* 187:265–77). Three direct repeats of a 10 bp sequence occur immediately downstream of the putative RBS sequence at positions 781–790, 795–804 and 810–817, and are boxed in FIG. 1. Nucleotides 710–725 are underlined because they are homologous to the palindromic regulatory sequence first found by Cornell University which lies upstream of several cellulase genes isolated from *Thermomonospora fusca* (Lin and Wilson, 1988, *J. Bacteriol.* 170:3843–3846) and later in another Actinomycete bacterium, *Microbispora bispora* (Yablonsky et al. In *Biochemistry & Genetics of Cellulose Degradation;* Aubert, Beguin, Millet, Eds., Academic Press: New York, N.Y., 1988, pp 249–266).

Promoter sequences for the E1 endoglucanase gene are not readily defined. There is extreme diversity of promoter sequences in Streptomycete genes. However, it is believed that they probably reside between the putative upstream regulatory sequence (at 710–725) and the putative RBS (at 772–779). Regardless, the DNA sequence of FIG. 1 contains the promotor. Nucleotides 2514–2560 are underlined because they comprise a nearly perfect dyad which may function as a transcriptional terminator, as observed for other Streptomycete genes (Molnar, In *Recombinant Microbes for Industrial and Agricultural Applications*, Murooka and Imanaka, Eds., Marcel-Dekker, New York, N.Y., 1994).

FIG. 2 shows the putative signal sequence in lower case letters. An alternative signal sequence may begin at the methionine residue at position 14 in this sequence. The mature E1 protein begins at position 42. This has been demonstrated by N-terminal amino acid sequencing of the purified native E1 endoglucanase protein from culture supernatants of *Acidothermus cellulolyticus* (boxed). The underlined sequence in FIG. 2 resembles the proline/serine/threonine-rich linker domain common to multi-domain microbial cellulases. The sequences following the linker domain appear to comprise the cellulose binding domain (CBD). This sequence shows easily discernable, but not identical homology with CBD sequences from other cellulases. Sequences preceding the underlined linker domain appear to comprise the catalytic domain of the E1 endoglucanase. This catalytic domain sequence is similar to, but not identical to catalytic domain sequences from other bacterial cellulase proteins.

EXAMPLE 4

Expression of Truncated E1 Endoglucanase

When the E1 endoglucanase gene is expressed in *E. coli* a product of the gene which has a lower molecular weight than the native gene product, or that which is expressed in *S. lividans* is detected. The native and *S. lividans* products run at 72 kDa on SDS polyacrylamide gels, whereas the largest E1 product from *E. coli* runs at approximately 60 kDa. Positive identification of the predominant gene products was performed by Western blotting techniques, using a monoclonal antibody specific for the E1 endoglucanase. This monoclonal antibody does not cross react with any other protein in *E. coli*, *S. lividans* or *A. cellulolyticus*. The purified *E. coli* product and the N-terminus of the polypeptide was sequenced by automated Edman degradation. The sequence is identical to that of the purified native E1 protein from *A. cellulolyticus*. Accordingly, the recombinant E1 gene product from *E. coli* is carboxy-terminally truncated by some mechanism in this host system.

EXAMPLE 5

Modified E1 Endoglucanase Genes

The nucleotide sequence may be modified by random mutation or site specific mutation provided that the amino acid sequence is unchanged. In this manner, restriction endonuclease sites may be inserted or removed from the gene without altering the enzyme product. Additionally, certain host microorganisms are well known to prefer certain codons for enhanced expression. For example, Gouy et al, Nucleic Acids Research, 10(22): 7055–74 (1982). Any or all of the codons may be appropriately modified to enhanced expression. These changes constitute a conservative variant of the original DNA sequence.

Site specific mutation is a preferred method for inducing mutations in transcriptionally active genes (Kucherlapati, *Prog. in Nucl. Acid Res. and Mol. Biol.*, 36:301 (1989)). This technique of homologous recombination was developed as a method for introduction of specific mutations in a gene (Thomas et al., *Cell*, 44:419–428, 1986; Thomas and Capecchi, *Cell*, 51:503–512, 1987; Doetschman et al., *Proc. Natl. Acad. Sci.*, 85:8583–8587, 1988) or to correct specific mutations within defective genes (Doetschman et al., *Nature*, 330:576–578, 1987).

The nucleotide sequence may also be modified in the same manner to produce changes in the amino acid sequence. Similar techniques may be used in the present invention to alter the amino acid sequence to change a protease or other cleavage site, enhance expression or to change the biological properties of the enzyme. Small deletions and insertions may also be used to change the sequence. These changes constitute a variant in the amino acid sequence.

This group of variants are those in which at least one amino acid residue in the peptide molecule has been removed and a different residue inserted in its place. For a detailed description of protein chemistry and structure, see Schulz, G. E. et al., *Principles of Protein Structure*, Springer-Verlag, New York, 1978, and Creighton, T. E., *Proteins: Structure and Molecular Properties*, W. H. Freeman & Co., San Francisco, 1983. The types of substitutions which may be made in the protein or peptide molecule of the present invention may be based on analysis of the frequencies of amino acid changes between a homologous protein of different species, such as those presented in Table 1-2 of Schulz et al. (supra) and FIG. 3–9 of Creighton (supra). Based on such an analysis, conservative substitutions are defined herein as exchanges within one of the following five groups:

1. Small aliphatic, nonpolar or slightly polar residues: ala, ser, thr (pro, gly);
2. Polar, negatively charged residues and their amides: asp, asn, glu, gln;
3. Polar, positively charged residues: his, arg, lys;
4. Large aliphatic, nonpolar residues: met, leu, ile, val (cys); and
5. Large aromatic residues: phe, tyr, trp.

The three amino acid residues in parentheses above have special roles in protein architecture. Gly is the only residue lacking any side chain and thus imparts flexibility to the chain. Pro, because of its unusual geometry, tightly constrains the chain. Cys can participate in disulfide bond formation which is important in protein folding. Note the Schulz et al. would merge Groups 1 and 2, above. Note also that Tyr, because of its hydrogen bonding potential, has some kinship with Ser, Thr, etc. Substantial changes in functional properties are made by selecting substitutions that are less conservative, such as between, rather than within, the above five groups, which will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (a) substitution of gly and/or pro by another amino acid or deletion or insertion of gly or pro; (b) substitution of a hydrophilic residue, e.g., ser or thr, for (or by) a hydrophobic residue, e.g., leu, ile, phe, val or ala; (c) substitution of a cys residue for (or by) any other residue; (d) substitution of a residue having an electro-positive side chain, e.g., lys, arg or his, for (or by) a residue having an electronegative charge, e.g., glu or asp; or (e) substitution of a residue having a bulky side chain, e.g., phe, for (or by) a residue not having such a side chain, e.g., gly.

Most deletions and insertions, and substitutions according to the present invention are those which do not produce radical changes in the characteristics of the protein or peptide molecule. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the peptide molecule-encoding nucleic acid, expression of the variant nucleic acid in recombinant culture, and, optionally, purification from the culture, for example, by immunoaffinity chromatography using a specific antibody such as the monoclonal antibody used in Example 4, on a column (to absorb the variant by binding).

The activity of the microbial lysate or purified protein or peptide variant can be screened in a suitable screening assay for the desired characteristic. For example, the CMCase assay of Example 1 may be repeated with differing conditions to determine the enzyme activity under different conditions.

Modifications of such peptide properties as redox or thermal stability, hydrophobicity, susceptibility to proteolytic degradation, pH insensitivity, resistance to sheer stress, biological activity, expression yield, or the tendency to aggregate with carriers or into multimers are assayed by methods well known to the ordinarily skilled artisan.

EXAMPLE 6

Mixed Domain E1 Endoglucanase Genes and Hybrid Enzymes

From the putative locations of the domains in the E1 endoglucanase gene given above and in FIG. 3 and comparable cloned cellulase genes from other species, one can separate individual domains and rejoin them to one or more domains from different genes. The similarity between all of the endoglucanase genes permit one to ligate one or more domains from the *Acidothermus cellulolyticus* E1 endoglucanase gene with one or more domains from an endoglucanase gene from one or more other microorganisms. Other representative endoglucanase genes include *Bacillus polymyxa* β-1,4endoglucanase (Baird et al, Journal of Bacteriology, 172: 1576–86 (1992)) and *Xanthomonas campestsis* β-1,4-endoglucanase A (Gough et al, Gene 89:53–59 (1990)). The result of the fusion of the two domains will, upon expression, be a hybrid enzyme. For ease of manipulation, restriction enzyme sites may be previously added to the respective genes by site-specific mutagenesis. If one is not using one domain of a particular gene, any number of any type of change including complete deletion may be made in the unused domain for convenience of manipulation.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

All references mentioned in this application are incorporated by reference.

---

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

```
Ala  Gly  Gly  Gly  Tyr  Trp  His  Thr  Ser  Gly  Arg  Glu  Ile  Leu  Asp  Ala
  1                  5                          10                          15

Asn  Asn  Val  Pro  Val  Arg  Ile  Ala
                     2 0
```

(2) INFORMATION FOR SEQ ID NO:2:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:2:

```
Ala  Gly  Gly  Gly  Tyr  Trp  His  Thr  Ser  Gly  Arg  Glu  Ile  Leu  Asp  Ala
 1                    5                        10                       15

Asn  Asn  Val  Pro  Val  Arg  Ile  Ala  Gly  Ile  Asn  Trp  Phe  Gly  Phe  Glu
               20                        25                       30

Thr  Xaa  Asn  Tyr  Val  Val
          35
```

(2) INFORMATION FOR SEQ ID NO:3:

(i) SEQUENCE CHARACTERISTICS:
        (A) LENGTH: 521 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:3:

```
Ala  Gly  Gly  Gly  Tyr  Trp  His  Thr  Ser  Gly  Arg  Glu  Ile  Leu  Asp  Ala
 1                    5                        10                       15

Asn  Asn  Val  Pro  Val  Arg  Ile  Ala  Gly  Ile  Asn  Trp  Phe  Gly  Phe  Glu
               20                        25                       30

Thr  Cys  Asn  Tyr  Val  Val  His  Gly  Leu  Trp  Ser  Arg  Asp  Tyr  Arg  Ser
          35                        40                       45

Met  Leu  Asp  Gln  Ile  Lys  Ser  Leu  Gly  Tyr  Asn  Thr  Ile  Arg  Leu  Pro
     50                        55                       60

Tyr  Ser  Asp  Asp  Ile  Leu  Lys  Pro  Gly  Thr  Met  Pro  Asn  Ser  Ile  Asn
 65                        70                       75                       80

Phe  Tyr  Gln  Met  Asn  Gln  Asp  Leu  Gln  Gly  Leu  Thr  Ser  Leu  Gln  Val
                    85                        90                       95

Met  Asp  Lys  Ile  Val  Ala  Tyr  Ala  Gly  Gln  Ile  Gly  Leu  Arg  Ile  Ile
               100                       105                      110

Leu  Asp  Arg  His  Arg  Pro  Asp  Cys  Ser  Gly  Gln  Ser  Ala  Leu  Trp  Tyr
          115                       120                      125

Thr  Ser  Ser  Val  Ser  Glu  Ala  Thr  Trp  Ile  Ser  Asp  Leu  Gln  Ala  Leu
     130                       135                      140

Ala  Gln  Arg  Tyr  Lys  Gly  Asn  Pro  Thr  Val  Val  Gly  Phe  Asp  Leu  His
145                       150                       155                      160

Asn  Glu  Pro  His  Asp  Pro  Ala  Cys  Trp  Gly  Cys  Gly  Asp  Pro  Ser  Ile
               165                       170                      175
```

```
Asp  Trp  Arg  Leu  Ala  Ala  Glu  Arg  Ala  Gly  Asn  Ala  Val  Leu  Ser  Val
          180                      185                          190

Asn  Pro  Asn  Leu  Leu  Ile  Phe  Val  Glu  Gly  Val  Gln  Ser  Tyr  Asn  Gly
          195                 200                      205

Asp  Ser  Tyr  Trp  Trp  Gly  Gly  Asn  Leu  Gln  Gly  Ala  Gly  Gln  Tyr  Pro
     210                 215                      220

Val  Val  Leu  Asn  Val  Pro  Asn  Arg  Leu  Val  Tyr  Ser  Ala  His  Asp  Tyr
225                      230                 235                          240

Ala  Thr  Ser  Val  Tyr  Pro  Gln  Thr  Trp  Phe  Ser  Asp  Pro  Thr  Phe  Pro
                    245                      250                     255

Asn  Asn  Met  Pro  Gly  Ile  Trp  Asn  Lys  Asn  Trp  Gly  Tyr  Leu  Phe  Asn
               260                      265                     270

Gln  Asn  Ile  Ala  Pro  Val  Trp  Leu  Gly  Glu  Phe  Gly  Thr  Thr  Leu  Gln
          275                      280                     285

Ser  Thr  Thr  Asp  Gln  Thr  Trp  Leu  Lys  Thr  Leu  Val  Gln  Tyr  Leu  Arg
     290                      295                     300

Pro  Thr  Ala  Gln  Tyr  Gly  Ala  Asp  Ser  Phe  Gln  Trp  Thr  Phe  Trp  Ser
305                      310                     315                          320

Trp  Asn  Pro  Asp  Ser  Gly  Asp  Thr  Gly  Gly  Ile  Leu  Lys  Asp  Asp  Trp
                    325                      330                     335

Gln  Thr  Val  Asp  Thr  Val  Lys  Asp  Gly  Tyr  Leu  Ala  Pro  Ile  Lys  Ser
               340                      345                     350

Ser  Ile  Phe  Asp  Pro  Val  Gly  Ala  Ser  Ala  Ser  Pro  Ser  Ser  Gln  Pro
          355                      360                     365

Ser  Pro  Ser  Val  Ser  Pro  Ser  Pro  Ser  Pro  Ser  Pro  Ser  Ala  Ser  Arg
     370                      375                     380

Thr  Pro  Thr  Pro  Thr  Pro  Thr  Pro  Thr  Ala  Ser  Pro  Thr  Pro  Thr  Leu
385                      390                     395                          400

Thr  Pro  Thr  Ala  Thr  Pro  Thr  Pro  Thr  Ala  Ser  Pro  Thr  Pro  Ser  Pro
                    405                      410                          415

Thr  Ala  Ala  Ser  Gly  Ala  Arg  Cys  Thr  Ala  Ser  Tyr  Gln  Val  Asn  Ser
               420                      425                     430

Asp  Trp  Gly  Asn  Gly  Phe  Thr  Val  Thr  Val  Ala  Val  Thr  Asn  Ser  Gly
          435                      440                     445

Ser  Val  Ala  Thr  Lys  Thr  Trp  Thr  Val  Ser  Trp  Thr  Phe  Gly  Gly  Asn
     450                      455                     460

Gln  Thr  Ile  Thr  Asn  Ser  Trp  Asn  Ala  Ala  Val  Thr  Gln  Asn  Gly  Gln
465                      470                     475                          480

Ser  Val  Thr  Ala  Arg  Asn  Met  Ser  Tyr  Asn  Asn  Val  Ile  Gln  Pro  Gly
               485                      490                     495

Gln  Asn  Thr  Thr  Phe  Gly  Phe  Gln  Ala  Ser  Tyr  Thr  Gly  Ser  Asn  Ala
               500                      505                     510

Ala  Pro  Thr  Val  Ala  Cys  Ala  Ala  Ser
          515                      520
```

(2) INFORMATION FOR SEQ ID NO:4:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:4:

Met Leu Arg Val Gly Val Val Ala Val Leu Ala Leu Val Ala Ala
1               5                   10                  15

Leu Ala Asn Leu Ala Val Pro Arg Pro Ala Arg Ala
            20              25

( 2 ) INFORMATION FOR SEQ ID NO:5:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:5:

Val Pro Arg Ala Leu Arg Arg Val Pro Gly Ser Arg Val
1               5                   10

( 2 ) INFORMATION FOR SEQ ID NO:6:

( i ) SEQUENCE CHARACTERISTICS:
        ( A ) LENGTH: 3004 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:6:

```
GGATCCACGT TGTACAAGGT CACCTGTCCG TCGTTCTGGT AGAGCGGCGG GATGGTCACC     60
CGCACGATCT CTCCTTTGTT GATGTCGACG GTCACGTGGT TACGGTTTGC CTCGGCCGCG    120
ATTTTCGCGC TCGGGCTTGC TCCGGCTGTC GGGTTCGGTT TGGCGTGGTG TGCGGAGCAC    180
GCCGAGGCGA TCCCAATGAG GGCAAGGGCA AGAGCGGAGC CGATGGCACG TCGGGTGGCC    240
GATGGGGTAC GCCGATGGGG CGTGGCGTCC CCGCCGCGGA CAGAACCGGA TGCGGAATAG    300
GTCACGGTGC GACATGTTGC CGTACCGCGG ACCCGGATGA CAAGGGTGGG TGCGCGGGTC    360
GCCTGTGAGC TGCCGGCTGG CGTCTGGATC ATGGGAACGA TCCCACCATT CCCCGCAATC    420
GACGCGATCG GGAGCAGGGC GGCGCGAGCC GGACCGTGTG GTCGAGCCGG ACGATTCGCC    480
CATACGGTGC TGCAATGCCC AGCGCCATGT TGTCAATCCG CCAAATGCAG CAATGCACAC    540
ATGGACAGGG ATTGTGACTC TGAGTAATGA TTGGATTGCC TTCTTGCCGC CTACGCGTTA    600
CGCAGAGTAG GCGACTGTAT GCGGTAGGTT GGCGCTCCAG CCGTGGGCTG GACATGCCTG    660
CTGCGAACTC TTGACACGTC TGGTTGAACG CGCAATACTC CCAACACCGA TGGGATCGTT    720
CCCATAAGTT TCCGTCTCAC AACAGAATCG GTGCGCCCTC ATGATCAACG TGAAAGGAGT    780
ACGGGGGAGA ACAGACGGGG GAGAAACCAA CGGGGGATTG GCGGTGCCGC GCGCATTGCG    840
```

| | | | | | | |
|---|---|---|---|---|---|---|
| GCGAGTGCCT | GGCTCGCGGG | TGATGCTGCG | GGTCGGCGTC | GTCGTCGCGG | TGCTGGCATT | 900 |
| GGTTGCCGCA | CTCGCCAACC | TAGCCGTGCC | GCGGCCGGCT | CGCGCCGCGG | GCGGCGGCTA | 960 |
| TTGGCACACG | AGCGGCCGGG | AGATCCTGGA | CGCGAACAAC | GTGCCGGTAC | GGATCGCCGG | 1020 |
| CATCAACTGG | TTTGGGTTCG | AAACCTGCAA | TTACGTCGTG | CACGGTCTCT | GGTCACGCGA | 1080 |
| CTACCGCAGC | ATGCTCGACC | AGATAAAGTC | GCTCGGCTAC | AACACAATCC | GGCTGCCGTA | 1140 |
| CTCTGACGAC | ATTCTCAAGC | CGGGCACCAT | GCCGAACAGC | ATCAATTTTT | ACCAGATGAA | 1200 |
| TCAGGACCTG | CAGGGTCTGA | CGTCCTTGCA | GGTCATGGAC | AAAATCGTCG | CGTACGCCGG | 1260 |
| TCAGATCGGC | CTGCGCATCA | TTCTTGACCG | CCACCGACCG | GATTGCAGCG | GGCAGTCGGC | 1320 |
| GCTGTGGTAC | ACGAGCAGCG | TCTCGGAGGC | TACGTGGATT | CCGACCTGC | AAGCGCTGGC | 1380 |
| GCAGCGCTAC | AAGGGAAACC | CGACGGTCGT | CGGCTTTGAC | TTGCACAACG | AGCCGCATGA | 1440 |
| CCCGGCCTGC | TGGGGCTGCG | GCGATCCGAG | CATCGACTGG | CGATTGGCCG | CCGAGCGGGC | 1500 |
| CGGAAACGCC | GTGCTCTCGG | TGAATCCGAA | CCTGCTCATT | TTCGTCGAAG | GTGTGCAGAG | 1560 |
| CTACAACGGA | GACTCCTACT | GGTGGGGCGG | CAACCTGCAA | GGAGCCGGCC | AGTACCCGGT | 1620 |
| CGTGCTGAAC | GTGCCGAACC | GCCTGGTGTA | CTCGGCGCAC | GACTACGCGA | CGAGCGTCTA | 1680 |
| CCCGCAGACG | TGGTTCAGCG | ATCCGACCTT | CCCCAACAAC | ATGCCGGCA | TCTGGAACAA | 1740 |
| GAACTGGGGA | TACCTCTTCA | ATCAGAACAT | TGCACCGGTA | TGGCTGGGCG | AATTCGGTAC | 1800 |
| GACACTGCAA | TCCACGACCG | ACCAGACGTG | GCTGAAGACG | CTCGTCCAGT | ACCTACGGCC | 1860 |
| GACCGCGCAA | TACGGTGCGG | ACAGCTTCCA | GTGGACCTTC | TGGTCCTGGA | ACCCCGATTC | 1920 |
| CGGCGACACA | GGAGGAATTC | TCAAGGATGA | CTGGCAGACG | GTCGACACAG | TAAAAGACGG | 1980 |
| CTATCTCGCG | CCGATCAAGT | CGTCGATTTT | CGATCCTGTC | GGCGCGTCTG | CATCGCCTAG | 2040 |
| CAGTCAACCG | TCCCCGTCGG | TGTCGCCGTC | TCCGTCGCCG | AGCCCGTCGG | CGAGTCGGAC | 2100 |
| GCCGACGCCT | ACTCCGACGC | CGACAGCCAG | CCCGACGCCA | ACGCTGACCC | CTACTGCTAC | 2160 |
| GCCCACGCCC | ACGGCAAGCC | CGACGCCGTC | ACCGACGGCA | GCCTCCGGAG | CCCGCTGCAC | 2220 |
| CGCGAGTTAC | CAGGTCAACA | GCGATTGGGG | CAATGGCTTC | ACGGTAACGG | TGGCCGTGAC | 2280 |
| AAATTCCGGA | TCCGTCGCGA | CCAAGACATG | GACGGTCAGT | TGGACATTCG | GCGGAAATCA | 2340 |
| GACGATTACC | AATTCGTGGA | ATGCAGCGGT | CACGCAGAAC | GGTCAGTCGG | TAACGGCTCG | 2400 |
| GAATATGAGT | TATAACAACG | TGATTCAGCC | TGGTCAGAAC | ACCACGTTCG | GATTCCAGGC | 2460 |
| GAGCTATACC | GGAAGCAACG | CGGCACCGAC | AGTCGCCTGC | GCAGCAAGTT | AATACGTCGG | 2520 |
| GGAGCCGACG | GGAGGGTCCG | GACCGTCGGT | TCCCCGGCTT | CCACCTATGG | AGCGAACCCA | 2580 |
| ACAATCCGGA | CGGAACTGCA | GGTACCAGAG | AGGAACGACA | CGAATGCCCG | CCATCTCAAA | 2640 |
| ACGGCTGCGA | GCCGGCGTCC | TCGCCGGGGC | GGTGAGCATC | GCAGCCTCCA | TCGTGCCGCT | 2700 |
| GGCGATGCAG | CATCCTGCCA | TCGCCGCGAC | GCACGTCGAC | AATCCCTATG | CGGGAGCGAC | 2760 |
| CTTCTTCGTC | AACCCGTACT | GGGCGCAAGA | AGTACAGAGC | GAACGGCGAA | CCAGACCAAT | 2820 |
| GCCACTCTCG | CAGCGAAAAT | GCGCGTCGTT | TCCACATATT | CGACGGCCGT | CTGGATGGAC | 2880 |
| CGCATCGCTG | CGATCAACGG | CGTCAACGGC | GGACCCGGCT | TGACGACATA | TCTGGACGCC | 2940 |
| GCCCTCTCCC | AGCAGCAGGG | AACCACCCCT | GAAGTCATTG | AGATTGTCAT | CTACGATCTG | 3000 |
| CCGG | | | | | | 3004 |

We claim:
1. A DNA comprising a DNA encoding the following amino acid sequence:
AGGGYWHTSGREILDANNVPVRIAGINWFGFETCN-YVVHGLWSRDYRSMLDQIKSLGYNTIR-LPYSDDILKPGTMPNSINFYQMNQDLQGLTSLQVM-DKIVAYAGQIGLRIILDRHRPDCSGQS ALWYTSSVSEATWISDLQALAQRYKGNPTVVGFDL-HNEPHDPACWGCGDPSIDWRLAAERAG NAVLSVNPNLLIFVEGVQSYNGDSYWWGGNLQGA-

GQYPVVLNVPNRLVYSAHDYATSVYPQT WFSDPTFPNNMPGIWNKNWGYLFNQNIAPVWLGEFGTTLQSTTDQTWLKTLVQYLRPTAQYG ADSFQWTFWSWNPDSGDTGGILKDDWQTVDTVKDGYLAPIKSSIFDPVGASASPSSQPSPSV SPSPSPSPSASRTPTPTPTPTASPTPTLTPTATPTPTASPTPSPTAASGARCTASYQVNSDW GNGFTVTVAVTNSGSVATKTWTVSWTFGGNQTITNSWNAAVTQNGQSVTARNMSYNNVIQPG QNTTFGFQASYTGSNAAPTVACAAS (SEQ ID NO:3).

2. The DNA according to claim 1 further comprising the following sequence attached to an amino terminal end:

MLRVGVVVAVLALVAALANLAVPRPARA, (SEQ ID NO:4).

3. The DNA according to claim 2 further comprising the following sequence attached to an amino terminal end:

VPRALRRVPGSRV, SEQ ID NO:5.

4. The DNA according to claim 1 comprising the following sequence:

| | | | | | | |
|---|---|---|---|---|---|---|
| GGATCCACGT | TGTACAAGGT | CACCTGTCCG | TCGTTCTGGT | AGAGCGGCGG | | 50 |
| GATGGTCACC | CGCACGATCT | CTCCTTTGTT | GATGTCGACG | GTCACGTGGT | | 100 |
| TACGGTTTGC | CTCGGCCGCG | ATTTTCGCGC | TCGGGCTTGC | TCCGGCTGTC | | 150 |
| GGGTTCGGTT | TGGCGTGGTG | TGCGGAGCAC | GCCGAGGCGA | TCCCAATGAG | | 200 |
| GGCAAGGGCA | AGAGCGGAGC | CGATGGCACG | TCGGGTGGCC | GATGGGGTAC | | 250 |
| GCCGATGGGG | CGTGGCGTCC | CCGCCGCGGA | CAGAACCGGA | TGCGGAATAG | | 300 |
| GTCACGGTGC | GACATGTTGC | CGTACCGCGG | ACCCGGATGA | CAAGGGTGGG | | 350 |
| TGCGCGGGTC | GCCTGTGAGC | TGCCGGCTGG | CGTCTGGATC | ATGGGAACGA | | 400 |
| TCCCACCATT | CCCCGCAATC | GACGCGATCG | GGAGCAGGGC | GGCGCGAGCC | | 450 |
| GGACCGTGTG | GTCGAGCCGG | ACGATTCGCC | CATACGGTGC | TGCAATGCCC | | 500 |
| AGCGCCATGT | TGTCAATCCG | CCAAATGCAG | CAATGCACAC | ATGGACAGGG | | 550 |
| ATTGTGACTC | TGAGTAATGA | TTGGATTGCC | TTCTTGCCGC | CTACGCGTTA | | 600 |
| CGCAGAGTAG | GCGACTGTAT | GCGGTAGGTT | GGCGCTCCAG | CCGTGGGCTG | | 650 |
| GACATGCCTG | CTGCGAACTC | TTGACACGTC | TGGTTGAACG | CGCAATACTC | | 700 |
| CCAACACCGA | TGGGATCGTT | CCCATAAGTT | TCCGTCTCAC | AACAGAATCG | | 750 |
| GTGCGCCCTC | ATGATCAACG | TGAAAGGAGT | ACGGGGGAGA | ACAGACGGGG | | 800 |
| GAGAAACCAA | CGGGGGATTG | GCGGTGCCGC | GCGCATTGCG | GCGAGTGCCT | | 850 |
| GGCTCGCGGG | TGATGCTGCG | GGTCGGCGTC | GTCGTCGCGG | TGCTGGCATT | | 900 |
| GGTTGCCGCA | CTCGCCAACC | TAGCCGTGCC | GCGGCCGGCT | CGCGCCGCGG | | 950 |
| GCGGCGGCTA | TTGGCACACG | AGCGGCCGGG | AGATCCTGGA | CGCGAACAAC | | 1000 |
| GTGCCGGTAC | GGATCGCCGG | CATCAACTGG | TTTGGGTTCG | AAACCTGCAA | | 1050 |
| TTACGTCGTG | CACGGTCTCT | GGTCACGCGA | CTACCGCAGC | ATGCTCGACC | | 1100 |
| AGATAAAGTC | GCTCGGCTAC | AACACAATCC | GGCTGCCGTA | CTCTGACGAC | | 1150 |
| ATTCTCAAGC | CGGGCACCAT | GCCGAACAGC | ATCAATTTTT | ACCAGATGAA | | 1200 |
| TCAGGACCTG | CAGGGTCTGA | CGTCCTTGCA | GGTCATGGAC | AAAATCGTCG | | 1250 |
| CGTACGCCGG | TCAGATCGGC | CTGCGCATCA | TTCTTGACCG | CCACCGACCG | | 1300 |
| GATTGCAGCG | GGCAGTCGGC | GCTGTGGTAC | ACGAGCAGCG | TCTCGGAGGC | | 1350 |
| TACGTGGATT | TCCGACCTGC | AAGCGCTGGC | GCAGCGCTAC | AAGGGAAACC | | 1400 |
| CGACGGTCGT | CGGCTTTGAC | TTGCACAACG | AGCCGCATGA | CCCGGCCTGC | | 1450 |
| TGGGGCTGCG | GCGATCCGAG | CATCGACTGG | CGATTGGCCG | CCGAGCGGGC | | 1500 |
| CGGAAACGCC | GTGCTCTCGG | TGAATCCGAA | CCTGCTCATT | TTCGTCGAAG | | 1550 |
| GTGTGCAGAG | CTACAACGGA | GACTCCTACT | GGTGGGGCGG | CAACCTGCAA | | 1600 |
| GGAGCCGGCC | AGTACCCGGT | CGTGCCGAACC | GTGCCGAACC | GCCTGGTGTA | | 1650 |
| CTCGGCGCAC | GACTACGCGA | CGAGCGTCTA | CCCGCAGACG | TGGTTCAGCG | | 1700 |
| ATCCGACCTT | CCCCAACAAC | ATGCCCGGCA | TCTGGAACAA | GAACTGGGGA | | 1750 |
| TACCTCTTCA | ATCAGAACAT | TGCACCGGTA | TGGCTGGGCG | AATTCGGTAC | | 1800 |
| GACACTGCAA | TCCACGACCG | ACCAGACGTG | GCTGAAGACG | CTCGTCCAGT | | 1850 |
| ACCTACGGCC | GACCGCGCAA | TACGGTGCGG | ACAGCTTCCA | GTGGACCTTC | | 1900 |
| TGGTCCTGGA | ACCCCGATTC | CGGCGACACA | GGAGGAATTC | TCAAGGATGA | | 1950 |
| CTGGCAGACG | GTCGACACAG | TAAAAGACGG | CTATCTCGCG | CCGATCAAGT | | 2000 |
| CGTCGATTTT | CGATCCTGTC | GGCGCGTCTG | CATCGCCTAG | CAGTCAACCG | | 2050 |
| TCCCCGTCGG | TGTCGCCGTC | TCCGTCGCCG | AGCCCGTCGG | CGAGTCGGAC | | 2100 |
| GCCGACGCCT | ACTCCGACGC | CGACAGCCAG | CCCGACGCCA | ACGCTGACCC | | 2150 |
| CTACTGCTAC | GCCCACGCCC | ACGGCAAGCC | CGACGCCGTC | ACCGACGGCA | | 2200 |
| GCCTCCGGAG | CCCGCTGCAC | CGCGAGTTAC | CAGGTCAACA | GCGATTGGGG | | 2250 |
| CAATGGCTTC | ACGGTAACGG | TGGCCGTGAC | AAATTCCGGA | TCCGTCGCGA | | 2300 |
| CCAAGACATG | GACGGTCAGT | TGGACATTCG | GCGGAAATCA | GACGATTACC | | 2350 |
| AATTCGTGGA | ATGCAGCGGT | CACGCAGAAC | GGTCAGTCGG | TAACGGCTCG | | 2400 |
| GAATATGAGT | TATAACAACG | TGATTCAGCC | TGGTCAGAAC | ACCACGTTCG | | 2450 |
| GATTCCAGGC | GAGCTATACC | GGAAGCAACG | CGGCACCGAC | AGTCGCCTGC | | 2500 |
| GCAGCAAGTT | AATACGTCGG | GGAGCCGACG | GGAGGGTCCG | GACCGTCGGT | | 2550 |
| TCCCCGGCTT | CCACCTATGG | AGCGAACCCA | ACAATCCGGA | CGGAACTGCA | | 2600 |
| GGTACCAGAG | AGGAACGACA | CGAATGCCCG | CCATCTCAAA | ACGGCTGCGA | | 2650 |
| GCCGGCGTCC | TCGCCGGGGC | GGTGAGCATC | GCAGCCTCCA | TCGTGCCGCT | | 2700 |
| GGCGATGCAG | CATCCTGCCA | TCGCCGCGAC | GCACGTCGAC | AATCCCTATG | | 2750 |
| CGGGAGCGAC | CTTCTTCGTC | AACCCGTACT | GGGCGCAAGA | AGTACAGAGC | | 2800 |
| GAACGGCGAA | CCAGACCAAT | GCCACTCTCG | CAGCGAAAAT | GCGCGTCGTT | | 2850 |
| TCCACATATT | CGACGGCCGT | CTGGATGGAC | CGCATCGCTG | CGATCAACGG | | 2900 |
| CGTCAACGGC | GGACCCGGCT | TGACGACATA | TCTGGACGCC | GCCCTCTCCC | | 2950 |
| AGCAGCAGGG CCGG | AACCACCCCT | GAAGTCATTG | AGATTGTCAT | CTACGATCTG | | 3000 |
| 3004 SEQ ID NO: 6. | | | | | | |

5. A vector comprising the DNA according to claim 1 and a vector sequence encoding either an origin of replication or an integration site for a host genome.

6. A vector according to claim 5 further comprising DNA encoding a signal sequence operably linked thereto.

7. A vector according to claim 5 further comprising exogenous regulatory sequences capable of causing expression of said DNA in a suitable host.

8. A recombinant microorganism containing the vector according to claim 5.

9. A recombinant microorganism containing the vector according to claim 6.

10. A recombinant microorganism containing the vector according to claim 7.

11. A recombinant microorganism according to claim 5 wherein a genus of said microorganism is selected from the group consisting of Saccharomyces, Streptomyces, Bacillus, Zymomonas and Escherichia.

12. A method for producing an endoglucanase comprising culturing the recombinant microorganism according to claim 8 in a vessel under culture conditions sufficient to express said DNA and recovering said endoglucanase therefrom.

13. The method according to claim 12, further comprising separating the recombinant microorganism from microbial medium and recovering said endoglucanase from the medium.

14. A method for producing an endoglucanase according to claim 12, further comprising effectively increasing the permeability of a membrane of the recombinant microorganism to permit release of said endoglucanase.

15. A DNA comprising at least one domain but not all of the domains of the *Acidothermus cellulolyticus* E1 endoglucanase.

16. The DNA according to claim 15 further comprising at least one domain from a cellulase gene other than E1 endoglucanase.

17. The DNA according to claim 16 wherein the DNA encodes a protein having a cellulase activity.

18. The DNA according to claim 17 wherein the cellulase activity is an endoglucanase activity.

* * * * *